United States Patent
Ferber et al.

(10) Patent No.: US 10,463,283 B2
(45) Date of Patent: Nov. 5, 2019

(54) SYSTEMS AND METHODS OF MULTISPECTRAL BLOOD MEASUREMENT

(71) Applicant: Spry Health, Inc., Palo Alto, CA (US)

(72) Inventors: Elad Ferber, Woodside, CA (US); Pierre-Jean Cobut, Menlo Park, CA (US)

(73) Assignee: Spry Health, Inc., Palo Alto, CA (US)

( * ) Notice: Subject to any disclaimer, the term of this patent is extended or adjusted under 35 U.S.C. 154(b) by 0 days.

(21) Appl. No.: 14/214,175

(22) Filed: Mar. 14, 2014

(65) Prior Publication Data

US 2014/0316226 A1     Oct. 23, 2014

Related U.S. Application Data

(60) Provisional application No. 61/785,417, filed on Mar. 14, 2013, provisional application No. 61/947,357, filed on Mar. 3, 2014.

(51) Int. Cl.
*A61B 5/1455* (2006.01)
*A61B 5/145* (2006.01)
(Continued)

(52) U.S. Cl.
CPC ........ *A61B 5/14532* (2013.01); *A61B 5/0022* (2013.01); *A61B 5/0205* (2013.01);
(Continued)

(58) Field of Classification Search
CPC ...... G01N 21/314; A61B 5/443; A61B 5/441; A61B 5/0059; A61B 5/0088; A61B 5/002;
(Continued)

(56) References Cited

U.S. PATENT DOCUMENTS 5,246,004 A * 9/1993 Clarke ............... A61B 5/14532
                                                600/322
5,435,309 A * 7/1995 Thomas ............. A61B 5/14532
                                                600/310
(Continued)

FOREIGN PATENT DOCUMENTS

WO          03071939          9/2003

OTHER PUBLICATIONS

International Application No. PCT/US2014/029575, International Search Report and Written Opinion dated Aug. 21, 2014.
(Continued)

*Primary Examiner* — Eric F Winakur
*Assistant Examiner* — Chu Chuan Liu
(74) *Attorney, Agent, or Firm* — Ahmann Kloke LLP

(57) ABSTRACT

An exemplary system comprises an energy transmitter, an energy receiver, and an analyzer. The energy transmitter may project energy at a first wavelength and a second wavelength into tissue of a user, the first wavelength and the second wavelength being associated with at least one nutrient of a set of nutrients in blood of the user. The energy receiver may generate a composite signal based on a fraction of the energy at the first wavelength and the second wavelength, the fraction of the energy being received through the tissue of the user. The analyzer may separate the composite signal into a first signal corresponding to the first wavelength and a second signal corresponding to the second wavelength, and detect, in the blood of the user, a concentration of the at least one nutrient of the set of nutrients based on the first signal and the second signal.

14 Claims, 8 Drawing Sheets

(51) Int. Cl.
*A61B 5/00* (2006.01)
*A61B 5/0205* (2006.01)
*G06F 19/00* (2018.01)
*G16H 40/67* (2018.01)

(52) U.S. Cl.
CPC ........ *A61B 5/1455* (2013.01); *A61B 5/14535* (2013.01); *A61B 5/14539* (2013.01); *G06F 19/00* (2013.01); *G16H 40/67* (2018.01); *A61B 5/681* (2013.01); *A61B 5/721* (2013.01); *A61B 5/743* (2013.01); *A61B 2560/045* (2013.01)

(58) Field of Classification Search
CPC ..... A61B 5/0205; A61B 5/145; A61B 5/1455; A61B 5/14551; A61B 5/14552; A61B 5/14532; A61B 5/72; A61B 5/14539; A61B 5/14535; A61B 5/0022; A61B 5/721; A61B 5/743
See application file for complete search history.

(56) References Cited

U.S. PATENT DOCUMENTS

| | | | | |
|---|---|---|---|---|
| 5,497,769 | A * | 3/1996 | Gratton | A61B 5/0059 356/41 |
| 5,770,454 | A * | 6/1998 | Essenpreis | A61B 5/14532 356/300 |
| 5,853,364 | A * | 12/1998 | Baker, Jr. | A61B 5/02416 600/300 |
| 9,713,428 | B2 * | 7/2017 | Chon | A61B 5/14551 |
| 2002/0065453 | A1 * | 5/2002 | Lesho | A61B 5/14532 600/347 |
| 2005/0148835 | A1 * | 7/2005 | Parker | A61B 5/14551 600/323 |
| 2007/0255122 | A1 | 11/2007 | Vol et al. | |
| 2008/0058622 | A1 * | 3/2008 | Baker | A61B 5/14552 600/344 |
| 2008/0091092 | A1 * | 4/2008 | Al-Ali | A61B 5/0002 600/310 |
| 2009/0154573 | A1 * | 6/2009 | Petersen | A61B 5/02028 375/257 |
| 2009/0312615 | A1 | 12/2009 | Caduff et al. | |
| 2010/0324384 | A1 * | 12/2010 | Moon | A61B 5/0245 600/323 |
| 2011/0046459 | A1 * | 2/2011 | Zhang | A61B 5/14553 600/310 |
| 2011/0087083 | A1 * | 4/2011 | Poeze | A61B 5/14532 600/316 |
| 2012/0059237 | A1 * | 3/2012 | Amir | A61B 5/0285 600/365 |
| 2012/0101351 | A1 | 4/2012 | Caduff et al. | |
| 2012/0184827 | A1 | 7/2012 | Shwartz et al. | |
| 2012/0253147 | A1 * | 10/2012 | Huiku | A61B 5/14551 600/310 |
| 2014/0200423 | A1 * | 7/2014 | Eisen | A61B 5/14551 600/340 |

OTHER PUBLICATIONS

European Patent Application No. 14770447.2 Search Report dated Oct. 26, 2016.

* cited by examiner

SYSTEMS AND METHODS OF MULTISPECTRAL BLOOD MEASUREMENT

CROSS-REFERENCE TO RELATED APPLICATIONS

The present application claims priority from U.S. Provisional Patent Application Ser. No. 61/785,417, filed Mar. 14, 2014, entitled "A Method and Devices to Monitor Health and Energy on a Semi-Continuous Basis using Active Multispectral and other Sensors to Improve Personal Health, Wellness, and Quality of Life," and U.S. Provisional Patent Application Ser. No. 61/947,357, filed Mar. 3, 2014, entitled "System and Methods for Blood Analytics Utilizing Wearable Sensors," which is incorporated herein by reference.

BACKGROUND

1. Technical Field

The present invention(s) generally relate to blood metrics measurements, and, more particularly, non-invasive apparatuses and methods of measuring blood metrics.

2. Description of Related Art

Wearable activity monitoring devices are growing in popularity. These devices aim to facilitate achieving a user's goal such as to lose weight, to increase physical activity, or simply to improve overall health. Many such devices may interface with computer software to allow visualization of the recorded data. Nevertheless, most devices are evolved cousins of pedometers, which measure the number of steps a user takes. Even though additional functions such as tallying the distance a user travels or calculating calorie consumptions may be added, these devices lack the ability to measure blood metrics.

SUMMARY

An exemplary system comprises an energy transmitter, an energy receiver, and an analyzer. The energy transmitter may project energy at a first wavelength and a second wavelength into tissue of a user, the first wavelength and the second wavelength being associated with at least one nutrient of a set of nutrients in blood of the user. The energy receiver may generate a composite signal based on a fraction of the energy at the first wavelength and the second wavelength, the fraction of the energy being received through the tissue of the user. The analyzer may separate the composite signal into a first signal corresponding to the first wavelength and a second signal corresponding to the second wavelength, and detect, in the blood of the user, a concentration of the at least one nutrient of the set of nutrients based on the first signal and the second signal.

The fraction of the energy may be received by the energy receiver after the fraction of the energy is reflected by the tissue of the user. The system may comprise a wearable member. The energy transmitter and the energy receiver may be secured to the wearable member such that the energy transmitter and the energy receiver are in contact or in proximity with the tissue. The analyzer may be further configured to determine a set of blood metrics based on the first signal and the second signal, the concentration of at least one nutrient of the set of nutrients being determined based on the determined set of blood metrics. The system may further comprise a user interface configured to display at least some of the set of blood metrics. The analyzer may be further configured to compare a blood metric of the set of blood metric to a threshold and to generate an alert if the blood metric exceeds the threshold. The set of blood metrics may comprise a blood glucose concentration.

The analyzer may be further configured to determine a first AC component and a first DC component of the first signal, to determine a second AC component and a second DC component of the second signal, wherein the concentration of a nutrient of the set of nutrients is detected based on the first AC component, the first DC component, the second AC component, and the second DC component. The system may further comprise a motion detector configured to measure a level of motion, and the analyzer is configured to compare the level of motion to a threshold and to discount a measurement of the composite signal when the level of motion exceeds the threshold. A nutrient of the set of nutrients may comprise glucose.

An exemplary method may comprise projecting energy at a first wavelength and a second wavelength into tissue of a user, the first wavelength and the second wavelength being associated with at least one nutrient of a set of nutrients in blood of the user, generating a composite signal based on a fraction of the energy at the first wavelength and the second wavelength, the fraction of the energy being received through the tissue of the user, separating the composite signal into a first signal corresponding to the first wavelength and a second signal corresponding to the second wavelength, and detecting, in the blood of the user, a concentration of the at least one nutrient of the set of nutrients based on the first signal and the second signal.

Another exemplary system may comprise an energy transmitter, an energy receiver, and an analyzer. The energy transmitter may be configured to project energy at a first wavelength and a second wavelength into tissue of a user, the first wavelength and the second wavelength being associated with, in blood of the user, at least component. The at least one component being at least one of one of glucose, hemoglobin, triglycerides, cholesterol, bilirubin, protein, albumin, blood pH, Hematocrit, cortisol, and/or electrolytes. The energy receiver may be configured to generate a composite signal based on a fraction of the energy at the first wavelength and the second wavelength, the fraction of the energy being received through the tissue of the user. The analyzer may be configured to separate the composite signal into a first signal corresponding to the first wavelength and a second signal corresponding to the second wavelength, and to detect, in the blood of the user, a concentration of the at least one component based on the first signal and the second signal.

Other features and aspects of various embodiments will become apparent from the following detailed description, taken in conjunction with the accompanying drawings, which illustrate, by way of example, the features of such embodiments.

BRIEF DESCRIPTION OF THE DRAWINGS

Various embodiments are described in detail with reference to the following figures. The drawings are provided for purposes of illustration only and merely depict some embodiments. These drawings shall not be considered limiting of the breadth, scope, or applicability of embodiments.

DETAILED DESCRIPTION

Biometrics including blood metrics may be measured by minimally invasive procedures to address medical conditions such as diabetes or in the diagnosis and discovery of diseases. Minimal-invasive procedure based devices may have the advantages of reducing costs and decreasing the need for invasive methods, thereby increasing the comfort and well-being of users and patients. Even though these devices have revolutionized patient care, they have only been described in, and approved for, medical purposes. Minimal-invasive procedure based devices are usually out of reach for the general public because they are designed for medical uses rather than non-medical purposes such as fitness, well-being, and quality of life.

Personal devices such as sphygmomanometers or pulse oximeters measure blood pressure or oxygen levels, respectively, on a per-request basis. They usually cannot measure blood metrics real time or periodically. Real-time blood metrics data (e.g., high resolution measurements, or measurements over long periods of time) may allow these devices to facilitate users monitoring and controlling their energy levels and/or metabolism. Nutritionists, people suffering from obesity, people desiring to eat healthier, fitness enthusiasts, semi-professional athletes, people likely to have hypoglycemia, or the vast majority of the general population can benefit from these devices.

In various embodiments, a multispectral blood metric measurement apparatus monitors blood metrics, fitness, and/or metabolism levels of various users in a non-invasive manner. The multispectral blood metric measurement apparatus may be, for example, wearable technology. The multispectral blood metric measurement apparatus may measure any number of blood metrics. Blood metrics may include, for example, various nutrient blood concentrations. Blood metrics may be, for example, monitored, stored, tracked, and/or analyzed.

Figure 1:
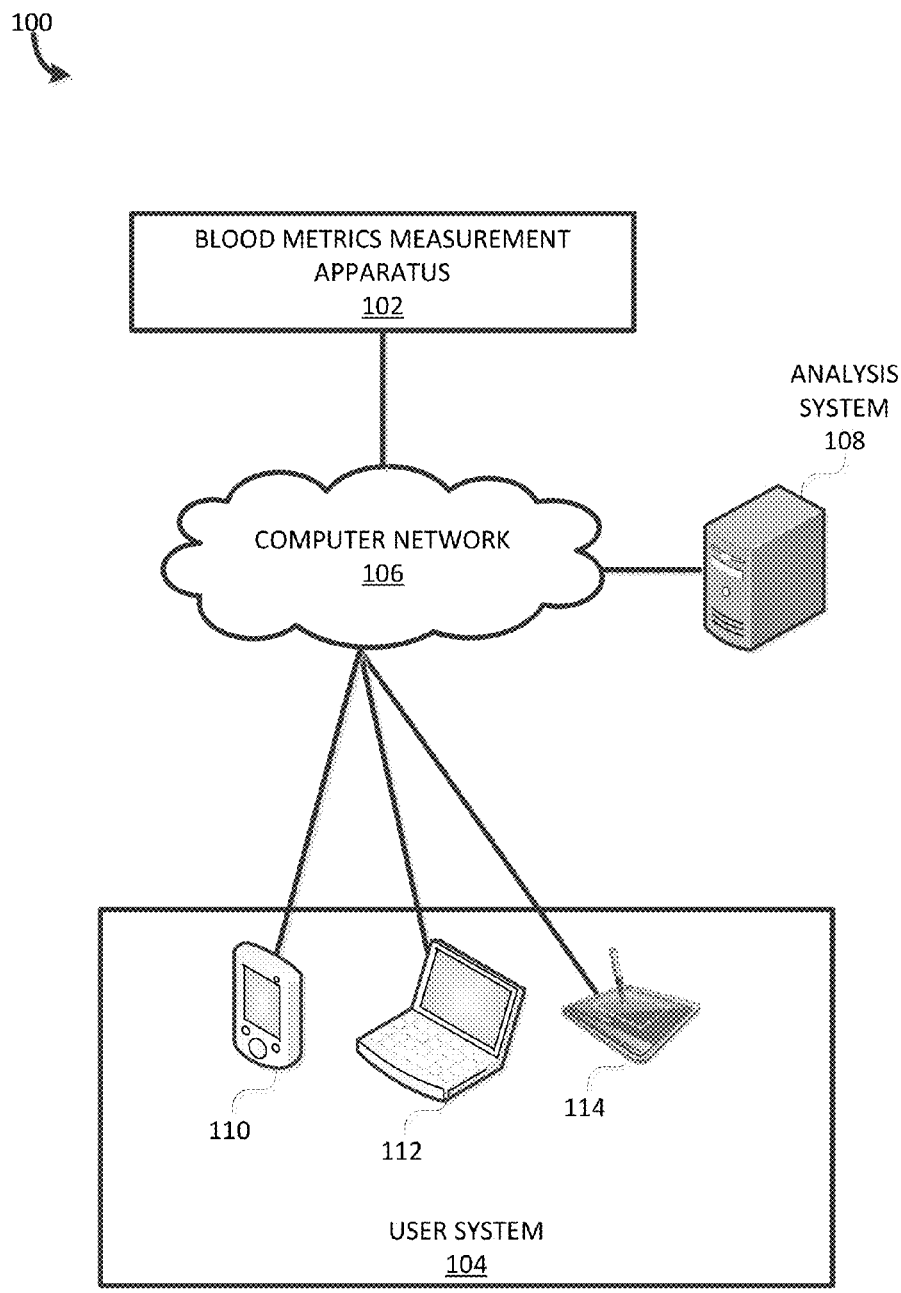
FIG. 1 is a block diagram illustrating an example environment utilizing a multispectral blood metrics measurement apparatus in accordance with various embodiments.

FIG. 1 is a block diagram illustrating an example environment 100 utilizing a multispectral blood metrics measurement apparatus 102 in accordance with various embodiments. As shown in FIG. 1, the example environment 100 may comprise a multispectral blood metrics measurement apparatus 102, one or more user systems 104, an optional analysis system 108, and a computer network 106 communicatively coupling together each of the multispectral blood metrics measurement apparatus 102, one or more user devices 110, 112, and 114 (depicted as user system 104), and/or the analysis system 108. As shown, a user system 108 may include a smartphone 110 (e.g., iPhone®), a computer 112 (e.g., a personal computer), and/or a tablet 114 (e.g., iPad®), through the computer network 106 (e.g., a Bluetooth® 4.0 personal area network), can either interact directly or indirectly with the blood metrics measurement apparatus 104.

The multispectral blood metrics measurement apparatus 102 may measure health or metabolism predictors non-invasively. The multispectral blood metrics measurement apparatus 102 may measure blood metrics such as concentrations of various nutrients over time, deliver energy into tissues of various body parts of a user, track a user's behavior pattern, detect motion, communicate various blood metric measurements, and/or receive a user's instructions. For instance, through the computer network 106, the multispectral blood metrics measurement apparatus 102 may transmit one or more blood metric measurements to, or receive instructions from, the user system 104 or the multispectral blood measurement system 108 such as which health or metabolism predictor to measure.

In some embodiments, the multispectral blood metric 102 measurement apparatus may project energy into tissue of a user and detect energy reflected from and/or transmitted through tissue of the user (e.g., the wearer of the multispectral blood metric measurement apparatus 102). The projected energy may be at multiple wavelengths that are associated with the blood metrics of interest to a user. The detected energy may be a fraction of the energy that is projected into the tissue. Energy at different wavelengths may be absorbed at a different rate that is related to a user's body state. The user's body state (e.g., heart rate, blood pressure, nutrient level, or the like) determines the amount of absorbed energy. Accordingly, energy at different wavelengths may be absorbed at different levels by a user's body. The fraction of energy received (e.g., that is reflected by the tissue or transmitted through the tissue) may be used to generate signals (e.g., composite signals) at different levels. These signals may provide information of the user's body state. This information may be obtained by analyzing waveforms of the signal in the time domain and/or the frequency domain.

In various embodiments, the multispectral blood metric measurement apparatus 102 may measure many metrics, including, but not limited to, skin conductivity, pulse, oxygen blood levels, blood pressure, blood glucose level, glycemic index, insulin index, Vvo2max, fat body composition, protein body composition, blood nutrient level (e.g., iron), body temperature, blood sodium levels, and/or naturally-produced chemical compound level (e.g., lactic acid). Nutrients may be determined based on the blood metrics to be measured. Nutrients may be measured may include, but are not limited to, glucose, hemoglobin, triglycerides, cholesterol, bilirubin, protein, albumin (i.e., egg white), and/or electrolytes (e.g., sodium, potassium, chloride, bicarbonate, etc.)

Those skilled in the art will appreciate that the user's body state may change dynamically and energy at a wavelength may be absorbed differently by a user over the time. By monitoring and tracking detected energy from the user's body, a user's health or condition may be more tracked. Systems and methods described herein may monitor and store blood metrics including concentrations of various nutrients. A user's history health records may be generated by using blood metrics measured at different times. In some embodiments, blood metrics measured a given time point may be compared to the history health records to detect any abnormal health conditions. The multispectral blood metric measurement apparatus may comprise a user interface where a user may input blood metrics of interest, be presented with various health reports, and/or be alerted with abnormal health conditions.

A user may comfortably wear a multispectral blood metric measurement apparatus 102 over time. The multispectral blood metric measurement apparatus 102 may comprise lightweight components. The multispectral blood metric measurement apparatus 102 may be made of hypoallergenic materials. The multispectral blood metric measurement apparatus 102 may be flexibly built so that it could fit various body parts (e.g., wrist, earlobe, ankle, or chest) of a user.

In accordance with some embodiments, the computer network 106 may be implemented or facilitated using one or more local or wide-area communications networks, such as the Internet, WiFi networks, WiMax networks, private networks, public networks, personal area networks ("PAN"), and the like. In some embodiments, the computer network 106 may be a wired network, such as a twisted pair wire system, a coaxial cable system, a fiber optic cable system, an Ethernet cable system, a wired PAN constructed with USB and/or FireWire connections, or other similar communication network. Alternatively, the computer network 106 may be a wireless network, such as a wireless personal area network, a wireless local area network, a cellular network, or other similar communication network. Depending on the embodiment, some or all of the communication connections with the computer network 106 may utilize encryption (e.g., Secure Sockets Layer [SSL]) to secure information being transferred between the various entities shown in the example environment 100.

Although FIG. 1 depicts a computer network 106 supporting communication between different digital devices, those skilled in the art will appreciate that the multispectral blood metrics measurement apparatus may be directly coupled (e.g., over a cable) with any or all of the user devices 110, 112, and 114.

The user devices 110-114 may include any digital device capable of executing an application related to measuring blood metrics, presenting an application user interface through a display and/or communicating with various entities in the example environment 100 through the computer network 106. For instance, through the computer network 106, the user device 110 may receive one or more blood metric measurements from the multispectral blood metrics measurement apparatus 102, track and store the blood metric measurements, analyze the blood metric measurements, and/or provide recommendations based on the blood metric measurements. An application user interface may facilitate interaction between a user of the user system 104 and an application running on the user system 104.

In various embodiments, any of user devices 110-114 may perform analysis of the measurements from the multispectral blood metrics measurement apparatus 102, display results, provide reports, display progress, display historic readings, track measurements, track analysis, provide alerts, and/or the like.

The analysis system 108 may be any form of digital device capable of executing an analysis application for analyzing and/or measuring blood metrics. In some embodiments, the analysis system 108 may generate reports or generate alerts based on analysis or measurement of blood metrics. For instance, through the computer network 106, the analysis system 108 may receive one or more blood metric measurements from the multispectral blood metrics measurement apparatus 102, track and store blood metric measurements, analyze blood metric measurements, and/or provide recommendations based on the analysis. An application programming interface may facilitate interaction between a user, the user devices 110-114, and/or the multispectral blood metrics measurement apparatus 110 with the analysis system 108.

Computing devices (e.g., digital devices) may include a mobile phone, a tablet computing device, a laptop, a desktop computer, personal digital assistant, a portable gaming unit, a wired gaming unit, a thin client, a set-top box, a portable multi-media player, or any other type of network accessible user device known to those of skill in the art. Further, the analysis system 108 may comprise of one or more servers, which may be operating on or implemented using one or more cloud-based services (e.g., System-as-a-Service [SaaS], Platform-as-a-Service [PaaS], or Infrastructure-as-a-Service [IaaS]).

It will be understood that for some embodiments, the components or the arrangement of components may differ from what is depicted in FIG. 1.

Each of the multispectral blood metrics measurement apparatus 102, one or more user devices 110, 112, and 114, and the analysis system 108 may be implemented using one or more digital devices. An exemplary digital device is described regarding FIG. 8.

Figure 2:
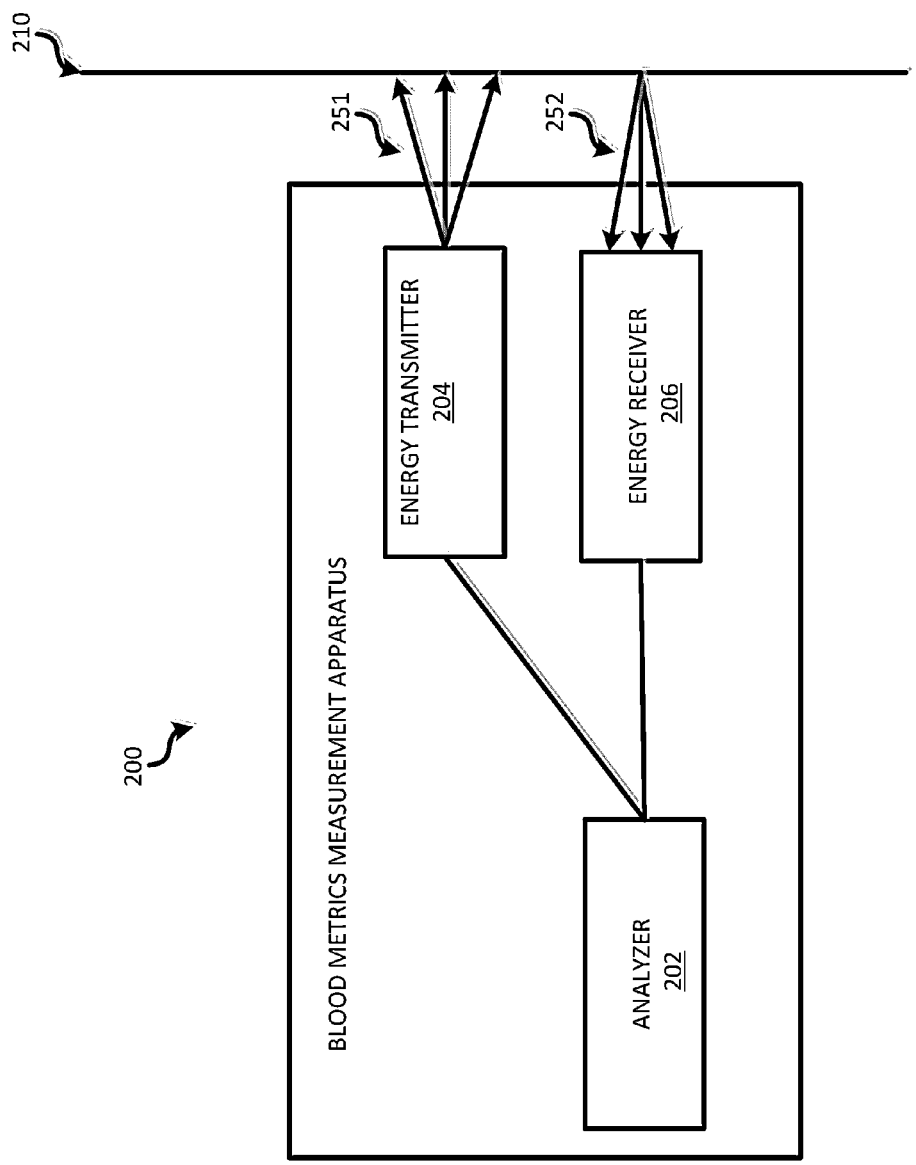
FIG. 2 is a block diagram illustrating an exemplary multispectral blood metrics measurement apparatus, such as the multispectral blood metrics measurement apparatus illustrated in FIG. 1

FIG. 2 is a block diagram illustrating an exemplary multispectral blood metrics measurement apparatus 200, such as the multispectral blood metrics measurement apparatus 102 illustrated in FIG. 1. The multispectral blood metrics measurement apparatus 200 comprises an analyzer 202, an energy transmitter 204, and an energy receiver 206. Various embodiments may comprise a wearable member. The wearable member may include, for example, a bracelet, glasses, necklace, ring, anklet, belt, broach, jewelry, clothing, or any other member of combination of members that allow the multispectral blood metrics measurement apparatus 200 to be close to or touch a body of the wearer.

The energy transmitter 204 and the energy receiver 206 may be secured to the wearable member such that the energy transmitter and the energy receiver may make contact or be in proximity with tissues (e.g., skin) of a user. The analyzer 202 may be coupled to the energy transmitter 204 and the energy receiver 206. In further embodiments, the multispectral blood metrics measurement apparatus 200 may comprise a communication module (not shown). The communication module may be coupled to the analyzer 202. The blood metrics measurement apparatus 200 may further comprise a driver (not shown) and a power source (not shown). The driver may be coupled to the energy transmitter 204 and the analyzer 202. The analyzer 202 may be coupled to the energy transmitter 204 via the driver. The power source may be coupled to the energy transmitter 204 via the driver. The blood metrics measurement apparatus 200 may further comprise an Analog-to-Digital Converter ("ADC") (not shown). The ADC may be coupled to the energy receiver 206 and the analyzer 202. In some embodiments, the blood metrics measurement apparatus 200 may comprise a motion sensor (e.g., an accelerometer, a global positioning system) (not shown). The motion sensor may be coupled to the analyzer 202.

In various embodiments, the energy transmitter 204 emits energy including, but not limited to, light, into the body of the user. The energy produced by the energy transmitter may be in the direction of entering tissues. For example, the energy produced by the energy transmitter 204 is in a direction 251 entering the tissue 210. In some embodiments, the energy transmitter 204 emits energy or light at different wavelengths. The energy transmitter 204 may comprise any number of light emission diodes ("LEDs"). In some embodiments, the energy transmitter 204 comprises at least two LEDs. Each LED may be configured to emit energy at one or more wavelengths. In another example, each LED may emit light with a peak wavelength centered around a wavelength. In one example, the energy transmitter 204 may emit light with a peak wavelength centered around 500 nm to 1800 nm.

Each wavelength may correspond to one or more blood metrics of interest and/or one or more nutrients. Those skilled in the art will appreciate that different components of the blood and/or different nutrients may absorb energy at different wavelengths. In various embodiments, a controller, driver, analyzer 202, or the like may receive a blood metric or nutrient of interest (e.g., from a user of the multispectral blood metrics measurement apparatus 200 and/or a user device not shown). The controller, driver, analyzer 202 or the like may associate the blood metric and/or nutrient of interest with one or more wavelengths and configure one or more of the LEDs to emit energy of at least one of the one or more wavelengths. For example, the analyzer 202 may command the driver to deliver electric power to one LED that is configured to emit light at the desired wavelength.

The energy receiver 206 may detect energy associated with the energy provided by the LEDs from tissues (e.g., skin) of the user. In this example, received and/or detected energy is in the direction 252 that leaves from the tissue 210. In various embodiments, the energy receiver 206 may detect energy from the body of the user that is a fraction of the energy produced by the energy transmitter 204.

The energy transmitter 204 and the energy receiver 206 may be configured such that the energy receiver 206 detects reflected energy from tissues of the user of the multispectral blood metrics measurement apparatus 200. For example, the energy transmitter 204 and the energy receiver 206 may be configured to be disposed on one surface or side of a user's tissue. The energy transmitter 204 and the energy receiver 206 may be configured such that the energy receiver 206 detects energy from the energy transmitter 204 that passes through or reflects from the user's tissues. In some embodiments, the energy transmitter 204 and the energy receiver 206 may be configured to be disposed on different (e.g., opposite) surfaces or sides of a users' tissue.

Energy detected from tissues of a user may be detected by the energy receiver 206. The energy receiver 206 may be configured to generate a signal in response to the detected energy. In some embodiments, the energy receiver 206 may be triggered by the energy received to generate an output which may be dependent or partially dependent upon the amount of energy received. The energy receiver 206 may be configured to generate a signal (e.g., an electric current, or an electric voltage) in response to the energy received from the tissues.

The signal generated by the energy receiver 206 may be associated with one or more blood metrics and/or nutrients of interest. Energy at different wavelengths may be absorbed at a different rate that is related to a user's body state. The user's body state (e.g., heart rate, blood pressure, nutrient level, or the like) may determine the amount of energy absorbed by the body. Accordingly, energy from the user's body at different wavelengths may be detected at different levels thereby causing different responses of the energy receiver 206. The energy receiver 206 may, for example, output signals based on the level of the energy received.

The energy receiver 206 may provide information associated with the user's body state. Blood metric information may be determined (e.g., by the analyzer 202) from the output signal of the energy receiver 206.

The energy receiver 206 may comprise a set of photodetectors (e.g., a photo diode, or a photo transistor) which are configured to output a signal dependent upon photons or the like from the energy transmitter 204 that passed through tissues of the user.

In various embodiments, the output signal of the energy receiver 206 is a composite of multiple signals. Each signal of the composite may be associated with energy at a wavelength which may be a portion (or fraction) of the total energy emitted by the energy transmitter 204.

The energy transmitter 204 may be configured to generate energy at a set of wavelengths. In some embodiments, the energy transmitter 204 is configured to generate energy such that energy at different wavelengths is generated sequentially and/or periodically. The energy transmitter 204 may be configured to generate energy at each particular wavelength until energy at all wavelengths of the set is generated. The period of time for the energy transmitter 204 to generate energy at all wavelengths is a generation period. Subsequent to completion of the generation period, the energy transmitter 204 may start a new generation period thereby allowing multiple measurements.

Figure 3:
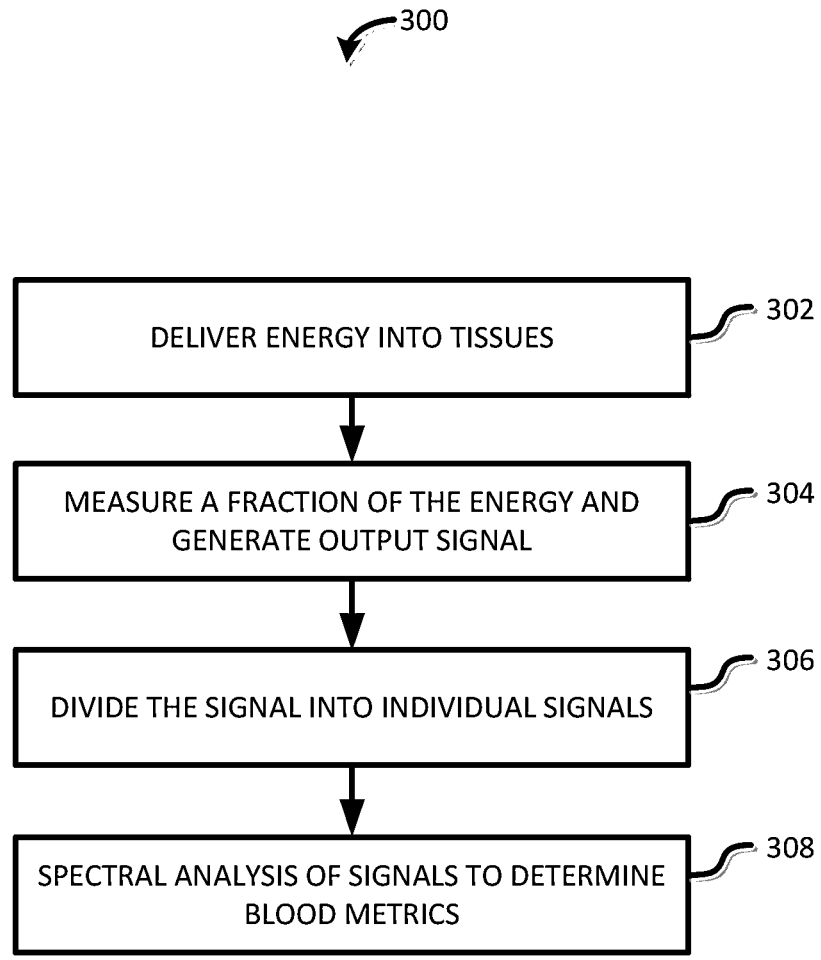
FIG. 3 illustrates an exemplary flow diagram of a method of measuring blood metrics in accordance with an embodiment of the present application.

FIG. 3 illustrates an exemplary flow diagram of a method 300 of measuring blood metrics in accordance with an embodiment of the present application. At step 302, energy transmitter 204 generates and delivers energy at different wavelengths into tissues (e g, skin) of a user. Different wavelengths may be associated with any number of nutrients, which may be associated with the blood metrics to be measured.

In some embodiments, a user may define various blood metrics and/or nutrients to be measured. Referring back to FIG. 1, a list of blood metrics and/or nutrients may be selected from a user interface (e.g., displayed on an interface of the multispectral blood metrics measurement apparatus 102, on a user device 110-114, or through the analysis system 108). The user may select one or more blood metrics and/or nutrients to be measured.

In some embodiments, a user may define a set of blood metrics to be measured on the user system 104; the multispectral blood metrics measurement apparatus 102 may provide the blood metrics to be measured to the user system 104. For example, on any device of the user system 104, a user may define one or more blood metrics by selecting one or more blood metrics from a list of blood metrics provided, for example, via the user interface.

As discussed herein, the multispectral blood metrics measurement apparatus 200 may measure, but is not limited to, skin conductivity, pulse, oxygen blood levels, blood pressure, blood glucose level, glycemic index, insulin index, Vvo2max, fat body composition, protein body composition, blood nutrient level (e.g., iron), body temperature, blood sodium levels, or naturally-produced chemical compound level (e.g., lactic acid). Nutrients may be determined based on the blood metrics to be measured. The multispectral blood metrics measurement apparatus 200 may measure nutrients, but is not limited to, glucose, hemoglobin, triglycerides, cholesterol, bilirubin, protein, albumin (i.e., egg white), or electrolytes (e.g., sodium, potassium, chloride, bicarbonate, or the like). The multispectral blood metrics measurement apparatus 200 may also measure oxygen, cortisol, and Hematocrit, for example (e.g., blood components).

In various embodiments, one or more wavelengths may be associated with a nutrient or a combination of blood components or molecules. In some embodiments, a number of wavelengths generated by the energy transmitter 204 are the number of blood components or molecules to be measured plus one. For example, when a total number of five (5) blood components and/or molecules are to be measured, a total number of six (6) wavelengths may be determined based on the blood components and/or molecules to be measured. Similarly, those skilled in the art will appreciate that one or more wavelengths may be associated with a nutrient or a combination of nutrients. In some embodiments, a number of wavelengths generated by the energy transmitter 204 are the number of nutrients to be measured plus one. For example, when a total number of three (3) nutrients are to be measured, a total number of four (4) wavelengths may be determined based on the nutrients to be measured.

In some embodiments, the multispectral blood metrics measurement apparatus 200, user devices 110-114, and/or analysis system 108 may comprise a reference table of blood components, molecules, and/or nutrients and wavelengths corresponding to the blood components, molecules, and/or nutrients. A wavelength may be unique to or more generally associated with a nutrient. A reference wavelength may be unique to or more generally associated with a combination of nutrients to be measured. As such, wavelength(s) may be determined by looking up each blood components, molecules, and/or nutrients that is to be measured. Energy at the determined wavelengths may be transmitted by the energy transmitter 204 into the body.

In various embodiments, in a predetermined time duration, energy at all desired wavelengths may be generated. For each wavelength, the corresponding energy may be generated for a time period equal to a predetermined time duration divided by the number of wavelengths. For example, four (4) wavelengths may be determined and the predetermined time duration is two (2) seconds. Accordingly, energy for each wavelength may be generated for a duration of half (0.5) second.

At step 304, the energy receiver 206 detects a fraction of the energy transmitted into the user's tissue by the energy transmitter 204. The energy receiver 206 may generate a signal based on the fraction of energy detected (e.g., based on the amount of the energy detected). In one example, energy detected at step 304 may be a fraction of the energy generated at step 302 reflected by the tissue. Energy detected at step 302 may be a fraction of the energy generated at step 302 that passes through the tissue (e.g., other undetected energy may be absorbed by tissue and/or otherwise blocked). The output signal of the energy receiver 206 may be an electric current or an electric voltage, of which the amplitude may be related to the amount of the energy detected. In various embodiments, steps 302 and 304 are performed simultaneously. That is, energy generation and detection may be performed approximately simultaneously.

In various embodiments, the output signal generated by the energy receiver 206 is a composite signal of multiple signals, each of which corresponds to one or more wavelengths. The output signal produced at step 306 may be divided into individual signals, each of which is may be associated with one or more wavelengths.

In various embodiments, analysis of the signals from the energy receiver 206 may identify abnormal measurements. For example, each of the measurement may be compared to a predetermined value. If the difference between the measurement and the predetermined value is above (or below) a threshold, then the measurement may be determined to be abnormal. An abnormal value may trigger additional analysis or an alert. In some embodiments, an abnormal value is ignored (e.g., as possibly effected by noise caused by movement of the energy transmitter 204 and/or the energy receiver 206). In various embodiments, the abnormal value may be discounted (e.g., the weight of the value reduced). The degree of discount may be based, for example, on information from an accelerometer (e.g., a large acceleration may indicate that the abnormal value should be significantly discounted) and/or based on historical values. Those skilled in the art will appreciate that the degree of discount may be based on any number of factors.

In some embodiments, measurements may be averaged over a period of time. A Kalman filer (e.g., a nonlinear, unscented Kalman filter) may be applied to any number of measurements or averaged measurements. A motion measurement (e.g., a measurement by an accelerometer) may be considered. Upon determining a measurement is abnormal, the motion measurement for that time point may be inspected. A large measurement may indicate large vibrations or accelerations that corroborate that the measurement may be abnormal. Measurements collected in such situations are likely to have significant electrical noises.

At step 308, the analyzer 202 may analyze signals from the energy receiver 206 analyzed in the frequency domain to determine blood metrics. Concentration of a nutrient in the blood may subsequently be determined. In some embodiments, signals may be provided to a bandpass filter that separates AC components from DC components. An AC component may represent signal variation at the cardiac frequency and a DC component may represent the average overall transmitted light intensity. In some embodiments, a heart rate and/or oxygen saturation, $SpO_2$ may be determined. The heart rate may be determined, for example, by averaging the maximum frequency to determine the rate of cardiac beats in a predetermined amount of time. The oxygen saturation $SpO_2$ may be determined according to Equation (1):

$$S_pO_2 = 110 - 25 \times R \quad (1),$$

where R is the ration of a red and infrared normalized transmitted light intensity. R may be determined according to Equation (2):

$$R = \frac{AC_R/DC_R}{AC_{IR}/DC_{IR}}, \quad (2),$$

where the $AC_R$ is the AC component of the detected energy corresponding to a wavelength (e.g., red light), $DC_R$ is the DC component of the detected energy corresponding to the wavelength (e.g., red light), $AC_{IR}$ is the AC component of the detected energy corresponding to a different wavelength (e.g., infrared light), and $DC_{IR}$ is the DC component of the detected energy corresponding to the different wavelength (e.g., infrared light). In some embodiments, the AC component may be selected as the highest spectral line in the cardiac frequency band. Waveform analysis may be performed to determine the R-R interval defined by two successive AC components, an elapsed interval and the probation, if there is any.

Those skilled in the art will appreciate that analysis may be performed by the analyzer 202 and/or any other digital device (e.g., any of users devices 110-114 or analysis system 108).

At step 308, state space estimation and progression may be performed to determine blood metrics. A system may be modeled according to Equation (3):

$$x(n+1)=f[x(n)]+u(n)$$

$$y(n)=h[x(n)]+v(n) \quad (3),$$

where x(n) represents the state of the system, u(n) is process noise, y(n) is the vector of the observed signals, and v(n) is the measurement noise.

Table 1 lists one or more parameters for x(n) as well as their initial value in some embodiments:

TABLE 1

| Parameter | Symbol | Initial Value |
|---|---|---|
| Cardiac frequency | $f_{HR}$ | 1 Hz |
| Cardiac phase | $\theta_{HR}$ | 0 |
| Cardiac harmonic amplitude | $I_{Harmonic}^{HR}$ | 0 |
| Cardiac Pulse Pressure | $P_{HR}$ | 1 |
| Point Blood Pressure | $P_{Point}$ | 1 |
| Respiratory frequency | $f_{Resp}$ | 0.3 Hz |
| Respiratory phase | $\theta_{Resp}$ | 0 |
| Wavelength i = 1 . . . N AC peak amplitude | $I_{\lambda_i}^{AC}$ | 0.5 max_value |
| Wavelength i = 1 . . . N AC peak location | $pos_{\lambda_i}^{AC}$ | Corresponding FFT bin to 1 Hz |
| Wavelength i = 1 . . . N DC | $I_{\lambda_i}^{DC}$ | 0.5 max_value |
| Wavelength i = 1 . . . N p2p amplitude | $I_{\lambda_i}^{p2p}$ | 1 ADC read |
| Wavelength i = 1 . . . N rise time | $\tau_{\lambda_i}^{rise}$ | 0.1 sec |
| Wavelength i = 1 . . . N Significance coefficient | $c_{\lambda_i}$ | 1 |
| Wavelength i = 1 . . . N HRV | $T_{\lambda_i}^{HRV}$ | 1 sec |
| Best Ratio pH | $BR_{pH}$ | 2 |
| Best Ratio pCO2 | $BR_{pCO2}$ | 3 |
| Best Ratio pHCO3- | $BR_{pHCO3-}$ | 4 |
| Acceleration magnitude | $I_{move}$ | 0 |
| GPS velocity | $|v|_{GPS}$ | 0 |
| GPS altitude | $|alt|_{GPS}$ | 0 |
| GPS acceleration | $|a|_{GPS}$ | 0 |
| GPS incline | $|incline|_{GPS}$ | 0 |
| Restfulness | Rest | 0 |
| Hydration | Hyd | 0 |

Table 2 lists one or more parameters for y(n) as well as their initial value in some embodiments:

TABLE 2

| Parameter | Symbol | Initial |
|---|---|---|
| Blood pH | pH | 7.35 |
| Blood PCO2 | $pCO_2$ | 24 mmol |
| Blood PO2 | $pO_2$ | 24 mmol |
| Blood PHCO3- | $pHCO_3^-$ | 24 mmol |
| Blood Glucose | $pC_6H_{12}O_6$ | 3 mmol |
| Cardiac Frequency | $f_{HR}$ | 1 |
| Point Blood Pressure | $P_{Point}$ | 1 |
| Respiratory Frequency | $f_{Resp}$ | 0.3 |
| GPS velocity | $|v|_{GPS}$ | 0 |
| GPS altitude | $|alt|_{GPS}$ | 0 |
| GPS acceleration | $|a|_{GPS}$ | 0 |
| GPS incline | $|incline|_{GPS}$ | 0 |

Table 3 lists the state space model F(X(n)) between the parameters listed in Table 1 and Table 2 in some embodiments, where the energy wavelengths comprise 880 nm, 631 nm, 1450 nm, and 1550 nm:

TABLE 3

| Name | Symbol | Equation |
|---|---|---|
| Cardiac frequency | $f_{HR}$ | $\text{bin\_to\_freq}\left(\frac{\Sigma c_{\lambda_i} pos_{\lambda_i}^{AC}}{\Sigma c_{\lambda_i}}\right)$ |
| Cardiac phase | $\theta_{HR}$ | $\theta_{HR}(n-1) + f_s^{-1} * \omega^*$, where $\omega^* \in [\omega\_min, \omega\_max]$ |
| Cardiac harmonic amplitude | $I_{Harmonic}^{HR}$ | $\frac{\Sigma c_{\lambda_i} I_{\lambda_i}^{p2p}}{\Sigma c_{\lambda_i}}$ |
| Cardiac Pulse Pressure | $P_{HR}$ | $\left(\frac{\Sigma c_{\lambda_i} \tau_{\lambda_i}^{rise}}{\Sigma c_{\lambda_i}}\right)^{\wedge} -1$ |
| Point Blood Pressure | $P_{Point}$ | $\tau_{\lambda_1}^{rise^{-1}}$ |
| Respiratory frequency | $f_{Resp}$ | 3) Respiratory and Heart Rate State Models: The fluctuations in the respiratory rate $\omega_r(n)$ and fluctuations in the heart rate $\omega_{ca}(n)$ that are not due to RSA are both modeled as a first-order autoregressive process with a mean and mild nonlinearity that limit the frequencies to know physiologic ranges |

$$\omega_r(n+1) = \overline{\omega}_r + \alpha_r \{s_r[\omega_r(n)] - \overline{\omega}_r\} + u_{\omega_r}(n) \quad (15)$$

$$\omega_{ca}(n+1) = \overline{\omega}_c + \alpha_c \{s_c[\omega_{ca}(n)] - \overline{\omega}_c\} + u_{\omega_{ca}}(n) \quad (16)$$

where $\overline{\omega}_r$ and $\overline{\omega}_c$ are the a priori estimates of the expected respiratory and cardiac frequencies, repectively; $\alpha_r$ and $\alpha_c$ control the bandwidth of the frequency fluctuations; and $u_{\omega_r}(n)$ and $u_{\omega_{ca}}(n)$ are white noise processes that model the random variation in the respiratory and cardiac frequencies, respectively. The instantaneous respiratory and heart rates in units of Hz are then $$f_r(n) = \frac{1}{2\pi T_s} s_r[\omega_r(n)] \quad (17)$$

$$f_c(n) = \frac{1}{2\pi T_s} s_c[\omega_c(n)]. \quad (18)$$

| Name | Symbol | Equation |
|---|---|---|
| Respiratory phase | $\theta_{Resp}$ | $\theta_{Resp}(n-1) + f_s^{-1} * \omega^*$, where $\omega^* \in [\omega\_min, \omega\_max]$ |
| \\lambda = 880 nm AC peak | $I_{\lambda_i}^{AC}$ | From FFT |
| \\lambda = 880 nm DC | $pos_{\lambda_i}^{AC}$ | From FFT |
| \\lambda = 880 nm p2p amplitude | $I_{\lambda_i}^{DC}$ | From Waveform analysis |
| \\lambda = 880 nm rise time | $I_{\lambda_i}^{p2p}$ | From Waveform analysis |
| \\lambda = 880 nm signal trend | $\tau_{\lambda_i}^{rise}$ | From Waveform analysis |

TABLE 3-continued

| Name | Symbol | Equation |
|---|---|---|
| $\lambda$ = 880 nm Significance coefficient | $c_{\lambda_i}$ | From Waveform analysis |
| $\lambda$ = 880 nm HRV | $T_{\lambda_i}^{HRV}$ | From Waveform analysis |
| $\lambda$ = 631 nm AC peak | $I_{\lambda_i}^{AC}$ | From Fast Fourier Transformation ("FFT") |
| $\lambda$ = 631 nm DC | $pos_{\lambda_i}^{AC}$ | From FFT |
| $\lambda$ = 631 nm p2p amplitude | $I_{\lambda_i}^{DC}$ | From Waveform analysis |
| $\lambda$ = 631 nm rise time | $I_{\lambda_i}^{p2p}$ | From Waveform analysis |
| $\lambda$ = 631 nm signal trend | $\tau_{\lambda_i}^{rise}$ | From Waveform analysis |
| $\lambda$ = 631 nm Significance coefficient | $c_{\lambda_i}$ | From Waveform analysis |
| $\lambda$ = 631 nm HRV | $T_{\lambda_i}^{HRV}$ | From Waveform analysis |
| $\lambda$ = 1450 nm AC peak | $I_{\lambda_i}^{AC}$ | From FFT |
| $\lambda$ = 1450 nm DC | $pos_{\lambda_i}^{AC}$ | From FFT |
| $\lambda$ = 1450 nm p2p amplitude | $I_{\lambda_i}^{DC}$ | From Waveform analysis |
| $\lambda$ = 1450 nm rise time | $I_{\lambda_i}^{p2p}$ | From Waveform analysis |
| $\lambda$ = 1450 nm signal trend | $\tau_{\lambda_i}^{rise}$ | From Waveform analysis |
| $\lambda$ = 1450 nm Significance coefficient | $c_{\lambda_i}$ | From Waveform analysis |
| $\lambda$ = 1450 nm HRV | $T_{\lambda_i}^{HRV}$ | From Waveform analysis |
| $\lambda$ = 1550 nm AC peak | $I_{\lambda_i}^{AC}$ | From FFT |
| $\lambda$ = 1550 nm DC | $pos_{\lambda_i}^{AC}$ | From FFT |
| $\lambda$ = 1550 nm p2p amplitude | $I_{\lambda_i}^{DC}$ | From Waveform analysis |
| $\lambda$ = 1550 nm rise time | $I_{\lambda_i}^{p2p}$ | From Waveform analysis |
| $\lambda$ = 1550 nm signal trend | $\tau_{\lambda_i}^{rise}$ | From Waveform analysis |
| $\lambda$ = 1550 nm Significance coefficient | $c_{\lambda_i}$ | From Waveform analysis |
| $\lambda$ = 1550 nm HRV | $T_{\lambda_i}^{HRV}$ | From Waveform analysis |
| Best Ratio pH | $BR_{pH}$ | Device Calibration |
| Best Ratio pCO2 | $BR_{pCO2}$ | Device Calibration |
| Best Ratio pHCO3- | $BR_{pHCO3^-}$ | Device Calibration |
| Acceleration magnitude | $I_{move}$ | From Accelerometer |
| GPS velocity | $|v|_{GPS}$ | From GPS |
| GPS altitude | $|alt|_{GPS}$ | From GPS |
| GPS acceleration | $|a|_{GPS}$ | From GPS |
| GPS incline | $|incline|_{GPS}$ | From GPS |

Table 4 lists Y(n)=H(x(n)):

TABLE 4

| Name | Symbol | Equation |
|---|---|---|
| Blood pH | pH | $6.1 + \log\left(\dfrac{pHCO_3^-}{0.03 pCO_2}\right)$ |
| Blood PCO2 | $pCO_2$ | $\dfrac{\epsilon_{Hb}^{CO_2} - \epsilon_{Hb}^{Hb} * I_{\lambda_{CO_2}}^{AC} * I_{\lambda_1}^{DC} / \left(I_{\lambda_1}^{AC} * I_{\lambda_{CO_2}}^{DC}\right)}{\epsilon_{Hb}^{CO_2} - \epsilon_{CO_2}^{CO_2} + \left(\epsilon_{CO_2}^{Hb} - \epsilon_{Hb}^{Hb}\right) * I_{\lambda_{CO_2}}^{AC} * I_{\lambda_1}^{DC} / \left(I_{\lambda_1}^{AC} * I_{\lambda_{CO_2}}^{DC}\right)}$ |
| Blood PO2 | $pO_2$ | $\dfrac{\epsilon_{Hb}^{O_2} - \epsilon_{Hb}^{Hb} * I_{\lambda_{O_2}}^{AC} * I_{\lambda_1}^{DC} / \left(I_{\lambda_1}^{AC} * I_{\lambda_{O_2}}^{DC}\right)}{\epsilon_{Hb}^{O_2} - \epsilon_{O_2}^{O_2} + \left(\epsilon_{O_2}^{Hb} - \epsilon_{Hb}^{Hb}\right) * I_{\lambda_{O_2}}^{AC} * I_{\lambda_1}^{DC} / \left(I_{\lambda_1}^{AC} * I_{\lambda_{O_2}}^{DC}\right)}$ |
| Blood PHCO3- | $pHCO_3^-$ | $\dfrac{\epsilon_{Hb}^{HCO_3^-} - \epsilon_{Hb}^{Hb} * I_{\lambda_{HCO_3^-}}^{AC} * I_{\lambda_1}^{DC} / \left(I_{\lambda_1}^{AC} * I_{\lambda_{HCO_3^-}}^{DC}\right)}{\epsilon_{Hb}^{HCO_3^-} - \epsilon_{HCO_3^-}^{HCO_3^-} + \left(\epsilon_{HCO_3^-}^{Hb} - \epsilon_{Hb}^{Hb}\right) * I_{\lambda_{HCO_3^-}}^{AC} * I_{\lambda_1}^{DC} / \left(I_{\lambda_1}^{AC} * I_{\lambda_{HCO_3^-}}^{DC}\right)}$ |

TABLE 4-continued

| Name | Symbol | Equation |
|---|---|---|
| Blood Glucose | $pC_6H_{12}O_6$ | As above |
| Cardiac Frequency | $f_{HR}$ | As in f(x(n)) |
| Point Blood Pressure | $P_{Point}$ | As in f(x(n)) |
| Respiratory Frequency | $f_{Resp}$ | As in f(x(n)) |
| GPS velocity | $|v|_{GPS}$ | As in f(x(n)) |
| GPS altitude | $|alt|_{GPS}$ | As in f(x(n)) |
| GPS acceleration | $|a|_{GPS}$ | As in f(x(n)) |
| GPS incline | $|incline|_{GPS}$ | As in f(x(n)) |

As illustrated in Tables 3 and 4, by generating energy at different wavelengths, one or more blood metrics may be determined from the detected energy. For example, cardiac frequency, cardiac phase, cardiac harmonic amplitude, cardiac pulse pressure, point blood pressure, respiratory frequency, respiratory phase, blood pH, blood pCO₂, blood pHCO₃₋, or blood glucose, may be determined.

Figure 4:
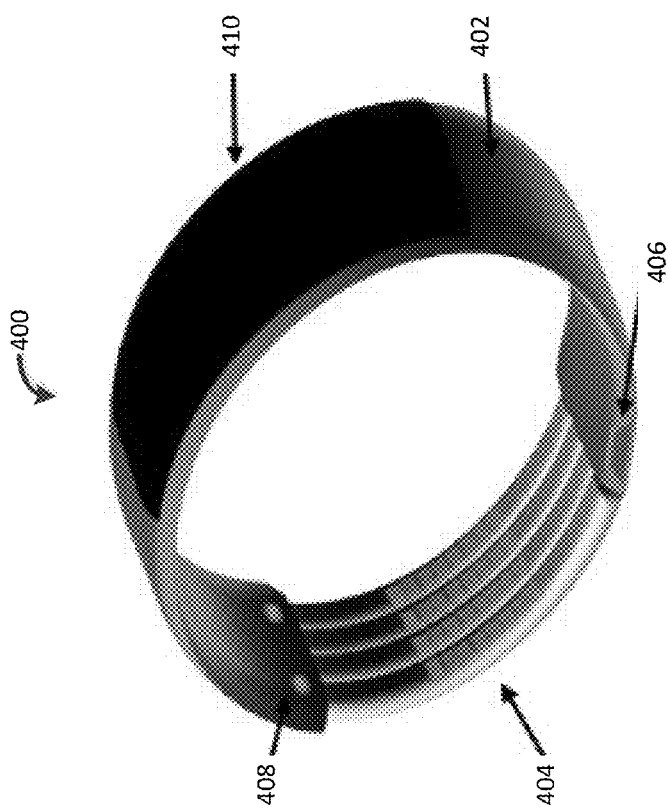
FIG. 4 illustrates an exemplary apparatus for measuring various blood metrics in accordance with an embodiment of the present application.

FIG. 4 illustrates an exemplary apparatus 400 for measuring various blood metrics in accordance with an embodiment of the present application. The apparatus 400 comprises a central unit 402, a sensor array 404, and a coupling means 408. The central unit 402 may be a wearable member made of elastic and/or flexible hypoallergenic wearable material.

In the illustrated example, the sensor array 404 is coupled to the central unit 402. The sensor array 404 may comprise any number of energy transmitters and/or energy receivers. The sensor array 404 may be detached from the central unit 402. In some embodiments, the sensor array 404 may be mechanically and electrically coupled to the central unit 402. The sensor array 404 comprises various illumination (e.g., near infra-red, infra-red, or short infra-red) and sensing array. The sensor array 404 may further comprise conductivity and/or capacity sensors. Different sensor array 404 may be provided to measure different blood metrics.

The central unit 402 may comprise an analyzer. In some embodiments, the central unit comprises an analyzer, one or more energy transmitter(s), and one or more energy receiver(s). The central unit 402 may further comprise a communication module and/or a battery compartment. The coupling means 408 are mounting screw holes in FIG. 4, however, those skilled in the art will appreciate that coupling means may be optional. Further, coupling means 408 may include any kind of means including a clip, hook, switch, expanding fabric, adhesive, or the like. One of ordinary skill in the art would understand that other mounting means may be used.

The apparatus 400 further comprises a micro-USB port 406 to allow for communication with a digital device and a screen 410. Various user interfaces (e.g., lights, a display, touchscreen, or the like) may be displayed on the screen 410.

Figure 5:
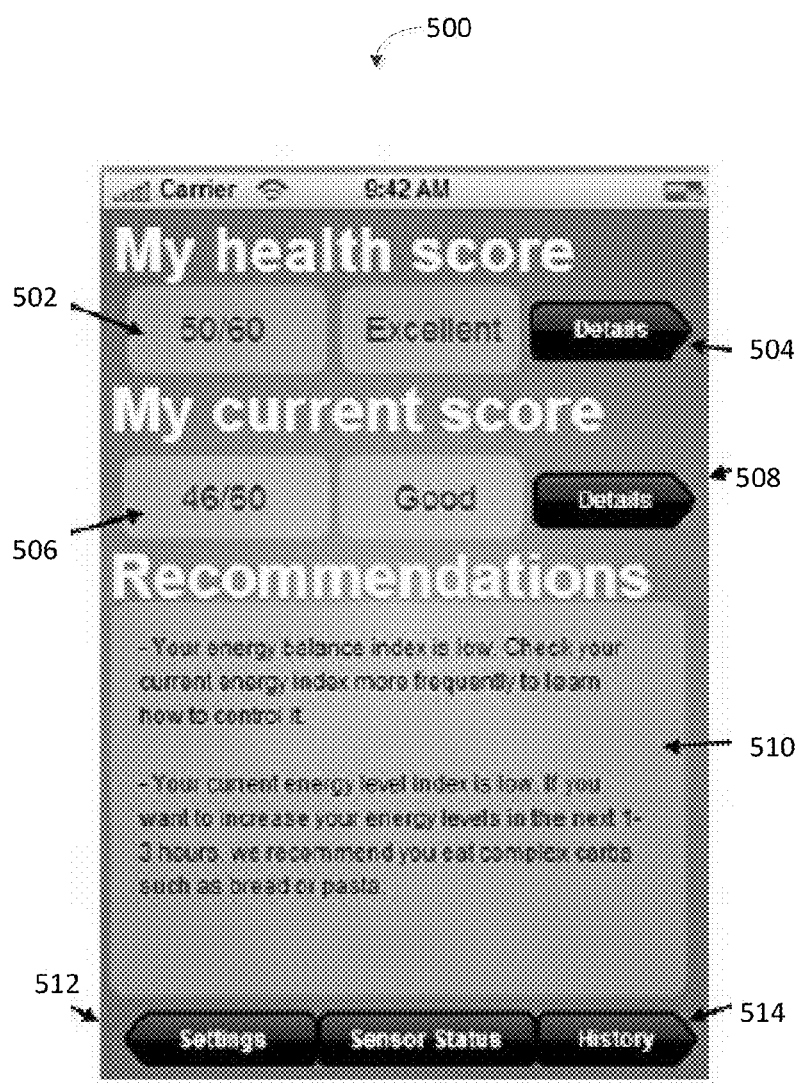
FIG. 5 illustrates a display of an assessment of a current health index derived from data collected from or with a multispectral blood metrics measurement apparatus in various embodiments
Figure 6:
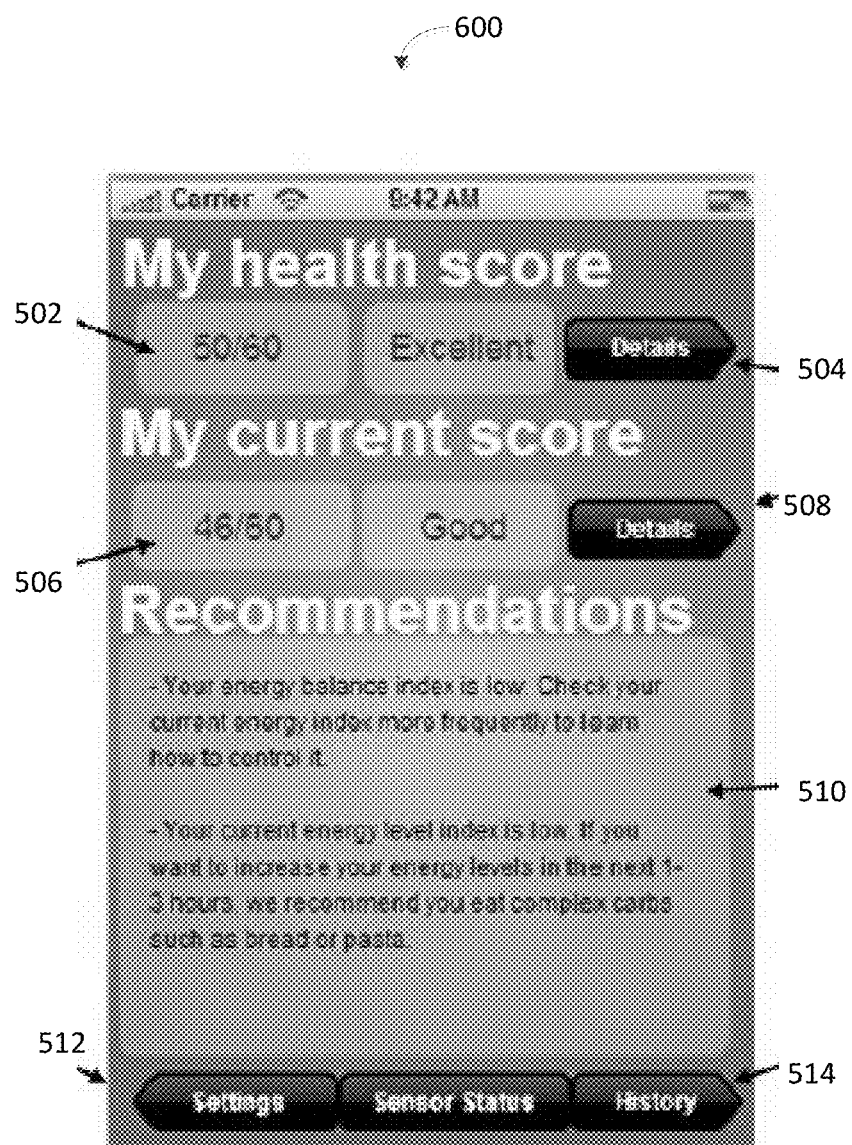
FIG. 6 illustrates a display of an assessment of an overall health index, derived from data collected from or with a multispectral blood metrics measurement apparatus in various embodiments.
Figure 7:
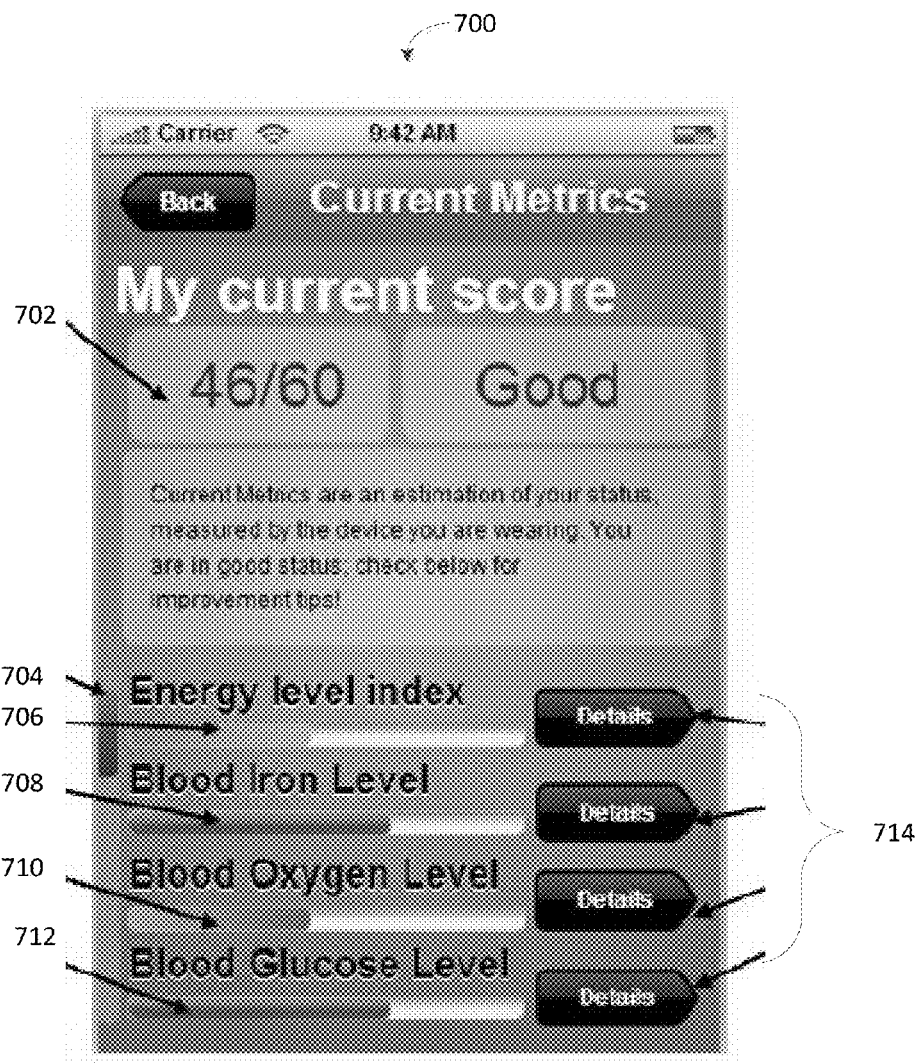
FIG. 7 illustrates a display of an assessment of an overall health index, derived from data collected from or with a multispectral blood metrics measurement apparatus in various embodiments.

FIGS. 5-7 are screenshots illustrating an example of presenting health analysis over a user interface in accordance with various embodiments. Various embodiments may store blood metrics and/or nutrient measurements. FIG. 5 illustrates a display 500 of an assessment of a current health index derived from data collected from or with a multispectral blood metrics measurement apparatus in various embodiments. The display may appear on the user's smartphone, for example. In various embodiments, the analyzer 202 or any digital device may analyze measurements collected over time to generate a health score that can be compared to a health threshold to provide qualitative and/or quantitative scoring. Similarly, the analyzer 202 or any digital device may analyze measurements recently collected to generate a current score that can be compared to a current health threshold to provide qualitative and/or quantitative scoring In some embodiments, a user interface may display a health score 502, an option for details regarding the health score 504, a current score 506, an option for details regarding the current score 508, a recommendation 510, a settings option 512, and a history of measurements 514. Options for details 504 and 506 may describe the metrics as well as the values of the metrics that went into the health score 504 and the current score 506, respectively.

In some embodiments, there is a recommendation engine configured to retrieve recommendations 510 based on the health score 504 and/or the current score 506. The settings option 512 may allow the user to configure metrics to be tracked and set alerts. In some embodiments, the user may utilize the settings options 512 to secure the information (e.g., encrypt the information and/or set passwords). The history of measurements option 514 may provide logged metrics and analysis information over time (e.g., as a chart).

Those skilled in the art will appreciate that the multispectral blood metrics measurement apparatus 200 and/or any digital device may generate reports based on the analysis, the metrics (e.g., blood metrics or metrics based on nutrients), historic measurements, historic analysis, or any other information. Further, alerts may be set by the multispectral blood metrics measurement apparatus 200 and/or any digital device.

Those skilled in the art will appreciate that the multispectral blood metrics measurement apparatus 200 may be taking many measurements over time (e.g., many measurements every minute) and may track health and changes in metrics over time and/or in the short term. In some embodiments, if a condition is of sufficient seriousness (e.g., heart rate shows erratic beats), the multispectral blood metrics measurement apparatus 200 or any digital device may provide an alert and request assistance (e.g., from emergency personnel via the communication network).

Various health and wellness predictors such as, but not limited to, energy level, blood iron level, blood oxygen level, and blood glucose level are displayed. FIG. 6 illustrates a display 600 of an assessment of an overall health index, derived from data collected from or with a multispectral blood metrics measurement apparatus in various embodiments.

In some embodiments, a user interface may display a current score 602, energy balance information 606, sleep quality information 608, blood metrics information 610, and body composition information 612 as well as other information accessible by slider 604. Additional details may be available through buttons 614. Those skilled in the art will appreciate that any amount of information may be provided. In some embodiments, the display 600 summarizes information while more detailed information recommendations, measurement data, analysis information, and the like may be available through the details buttons 614 or in other screens.

Recommendations to the user based on the current and previous measurements are provided. FIG. 7 illustrates a display 700 of an assessment of an overall health index, derived from data collected from or with a multispectral blood metrics measurement apparatus in various embodiments. In some embodiments, a user interface may display a current score 702, energy level information 706, blood iron level information 708, blood oxygen level information 710, and blood glucose level 712 as well as other information accessible by slider 704. Additional details may be available through buttons 714. Those skilled in the art will appreciate that any amount of information may be provided. In some embodiments, the display 700 summarizes information while more detailed information recommendations, measurement data, analysis information, and the like may be available through the details buttons 714 or in other screens.

Various embodiments track and analyze blood metrics. Health recommendations may be based on instantaneous blood metrics measurements and history blood metrics measurement. In addition, blood metrics and health condition of a user may be compared to health data of the general public. For example, a user's health condition may be compared to health condition of other similar users such as users of the same gender and age group, users of the same profession, friends of a user, etc.

Figure 8:
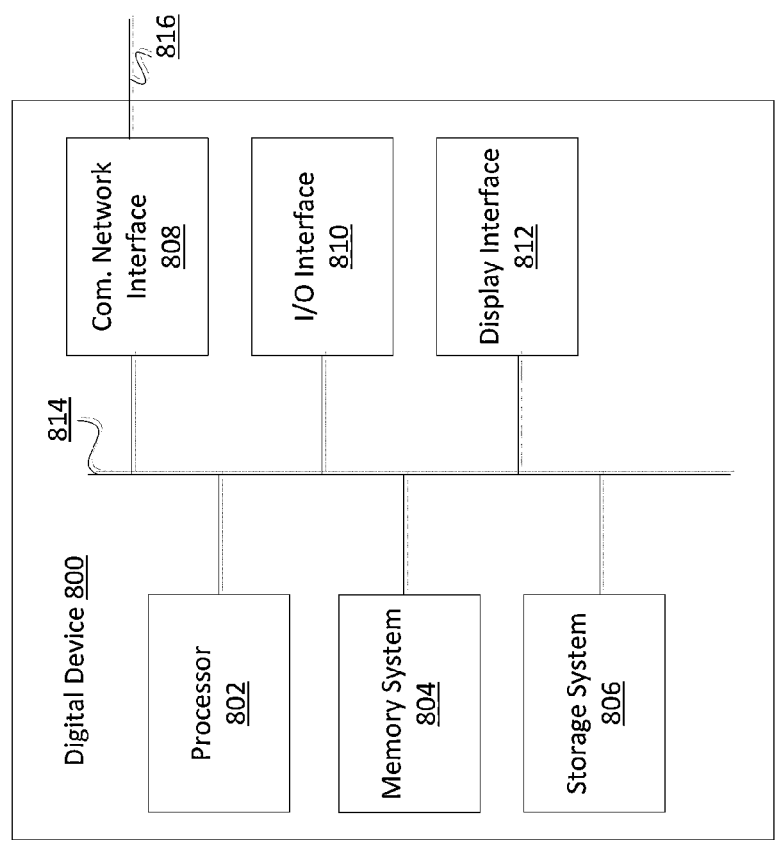
FIG. 8 is a block diagram illustrating an exemplary digital device that can be utilized in the implementation of various embodiments.

FIG. 8 is a block diagram of an exemplary digital device 800. The digital device 800 comprises a processor 802, a memory system 804, a storage system 806, a communication network interface 808, an I/O interface 810, and a display interface 812 communicatively coupled to a bus 814. The processor 802 is configured to execute executable instructions (e.g., programs). In some embodiments, the processor 802 comprises circuitry or any processor capable of processing the executable instructions.

The memory system 804 is any memory configured to store data. Some examples of the memory system 804 are storage devices, such as RAM or ROM. The memory system 804 can comprise the ram cache. In various embodiments, data is stored within the memory system 804. The data within the memory system 804 may be cleared or ultimately transferred to the storage system 806.

The storage system 806 is any storage configured to retrieve and store data. Some examples of the storage system 806 are flash drives, hard drives, optical drives, and/or magnetic tape. In some embodiments, the digital device 800 includes a memory system 804 in the form of RAM and a storage system 806 in the form of flash data. Both the memory system 804 and the storage system 806 comprise computer readable media which may store instructions or programs that are executable by a computer processor including the processor 802.

The communications network interface (com. network interface) 808 can be coupled to a network (e.g., the computer network 104) via the link 816. The communication network interface 808 may support communication over an Ethernet connection, a serial connection, a parallel connection, or an ATA connection, for example. The communication network interface 808 may also support wireless communication (e.g., 802.11 a/b/g/n, WiMax). It will be apparent to those skilled in the art that the communication network interface 808 can support many wired and wireless standards.

The optional input/output (I/O) interface 810 is any device that receives input from the user and output data. The optional display interface 812 is any device that is configured to output graphics and data to a display. In one example, the display interface 812 is a graphics adapter.

It will be appreciated by those skilled in the art that the hardware elements of the digital device 800 are not limited to those depicted in FIG. 8. A digital device 800 may comprise more or less hardware elements than those depicted. Further, hardware elements may share functionality and still be within various embodiments described herein. In one example, encoding and/or decoding may be performed by the processor 802 and/or a co-processor located on a GPU (i.e., Nvidia®).

The above-described functions and components can be comprised of instructions that are stored on a storage medium such as a computer readable medium. The instructions can be retrieved and executed by a processor. Some examples of instructions are software, program code, and firmware. Some examples of storage medium are memory devices, tape, disks, integrated circuits, and servers. The instructions are operational when executed by the processor to direct the processor to operate in accord with some embodiments. Those skilled in the art are familiar with instructions, processor(s), and storage medium.

Various embodiments are described herein as examples. It will be apparent to those skilled in the art that various modifications may be made and other embodiments can be used without departing from the broader scope of the invention(s) presented herein. These and other variations upon the exemplary embodiments are intended to be covered by the present invention(s).

What is claimed is:

1. A system comprising:
   a flexible wrist band;
   a plurality of light emitting diodes secured to the flexible wrist band, a first of the plurality of light emitting diodes configured to project energy at a first wavelength into tissue of a wearer and a second of the plurality of light emitting diodes configured to project energy at a second wavelength into the tissue of the wearer, the first wavelength and the second wavelength being associated with different analyte concentrations in blood of the wearer;
   at least one photo detector secured to the flexible wrist band, the at least one photo detector being adjacent to the plurality of light emitting diodes and configured to generate a composite signal based on a fraction of the energy at the first wavelength and the second wavelength, the fraction of the energy being reflected by the tissue of the wearer; and
   a processor configured to:
      separate the composite signal into a first signal corresponding to the first wavelength and a second signal corresponding to the second wavelength, and detect, in the blood of the wearer, a first analyte concentration measurement of a first analyte and a second analyte concentration measurement of a second analyte within the blood of the wearer based on the first signal and the second signal, respectively;

apply a Kalman filter to the first analyte concentration measurement and the second analyte concentration measurement;

compare a result of the application of the Kalman filter to the first analyte concentration measurement and the second analyte concentration measurement with at least one threshold associated with motion of the wearer to determine if at least the first analyte concentration measurement or the second analyte concentration measurement is abnormal as being influenced by the motion of the wearer;

if the first analyte concentration measurement and the second analyte concentration measurement are abnormal based on the comparison, remove abnormal measurements associated with the motion of the wearer; and if the first analyte concentration measurement and the second analyte concentration measurement are not determined to be abnormal based on the comparison, obtain a first analyte concentration of the first analyte and a second analyte concentration of the second analyte based at least on an assessment of the first analyte concentration measurement and a second analyte concentration measurement in a frequency domain.

2. The system of claim 1, wherein the processor is further configured to determine a set of blood metrics based on the first analyte concentration and the second analyte concentration.

3. The system of claim 2, further comprising a display coupled to the processor, the processor configured to display a user interface on the display, the user interface including at least some of the set of blood metrics.

4. The system of claim 2, wherein the processor is further configured to compare a blood metric of the set of blood metrics to a threshold and to generate an alert if the blood metric exceeds the threshold.

5. The system of claim 2, wherein the set of blood metrics comprises a blood glucose concentration.

6. The system of claim 1, wherein the processor is further configured to determine a first AC component and a first DC component of the first signal and to determine a second AC component and a second DC component of the second signal, wherein the first analyte concentration measurement is detected based on the first AC component and the first DC component, and the second analyte concentration measurement is detected based on the second AC component and the second DC component.

7. The system of claim 1, wherein the first analyte concentration measurement is a measurement of concentration of hemoglobin, triglyceride, bilirubin, protein, albumin, cortisol, or electrolyte.

8. A method comprising:
projecting a first wavelength of energy into tissue of a user;
projecting a second wavelength of energy into the tissue of the user, the first wavelength and the second wavelength being associated with different analyte concentrations in blood of the user;
receiving a fraction of the energy at the first and second wavelengths, the fraction of the energy being reflected by the tissue of the user;
generating a composite signal based on the fraction of the energy at the first wavelength and the second wavelength, the fraction of the energy being reflected by the tissue of the user;

separating, by a processor, the composite signal into a first signal corresponding to the first wavelength and a second signal corresponding to the second wavelength;

detecting, by a processor, a first analyte concentration measurement of a first analyte in the blood of the user based on the first wavelength and a second analyte concentration measurement of a second analyte in the blood of the wearer based on the second wavelength;

applying, by a processor, a Kalman filter to the first analyte concentration measurement and the second analyte concentration measurement;

comparing, by a processor, a result of the application of the Kalman filter to the first analyte concentration measurement and the second analyte concentration measurement with at least one threshold associated with motion of the wearer to determine if the at least the first analyte concentration measurement or the second analyte concentration measurement is abnormal as being influenced by the movement of the user;

if the first analyte concentration measurement and the second analyte concentration measurement are abnormal based on the comparison, remove abnormal measurements associated with movement by the user; and if the first analyte concentration measurement and the second analyte concentration measurement are not determined to be abnormal based on the comparison, obtain a first analyte concentration of the first analyte and a second analyte concentration of the second analyte based at least on an assessment of the first analyte concentration measurement and the second concentration measurement in a frequency domain.

9. The method of claim 8, further comprising displaying, on a display communicatively coupled to the processor the first analyte concentration measurement.

10. The method of claim 8, further comprising comparing the first analyte concentration to a threshold and generating an alert if the first analyte concentration exceeds the threshold.

11. The method of claim 8, wherein the first analyte concentration comprises a blood glucose concentration.

12. The method of claim 8, further comprising determining a first AC component and a first DC component of the first signal and determining a second AC component and a second DC component of the second signal, wherein the first analyte concentration measurement is detected based on the first AC component and the first DC component, and the second analyte concentration measurement is detected based on the second AC component and the second DC component.

13. The method of claim 8, wherein the first analyte concentration measurement is a measurement of concentration of hemoglobin, triglyceride, bilirubin, protein, albumin, cortisol, or electrolyte.

14. A system comprising:
a flexible wrist band;
a plurality of light emitting diodes secured to the flexible wrist band, a first of the plurality of light emitting diodes configured to project energy at a first wavelength into tissue of a wearer and a second of the plurality of light emitting diodes configured to project energy at a second wavelength into the tissue of the wearer, the first wavelength and the second wavelength being associated with different analyte concentrations in blood of the wearer, the different analyte concentrations being at least two selected from a set of components comprising hemoglobin, triglycerides, bilirubin, protein, albumin, blood pH, Hematocrit, cortisol, and electrolytes;

at least one photo detector secured to the flexible wrist band, the at least one photo detector being adjacent to the plurality of light emitting diodes and configured to generate a composite signal based on a fraction of the energy at the first wavelength and the second wavelength, the fraction of the energy being reflected by the tissue of the wearer; and a processor configured to:
  separate the composite signal into a first signal corresponding to the first wavelength and a second signal corresponding to the second wavelength, and to detect, in the blood of the wearer, a first analyte concentration measurement of a first analyte and a second analyte concentration measurement of a second analyte within the blood of the wearer based on the first signal and the second signal, respectively;
  apply a Kalman filter to the first analyte concentration measurement and the second analyte concentration measurement;
  compare a result of the application of the Kalman filter to the first analyte concentration measurement and the second analyte concentration measurement with at least one threshold associated with motion of the wearer to determine if at least the first analyte concentration measurement or the second analyte concentration measurement is abnormal as being influenced by the motion of the wearer;
  if the first analyte concentration measurement and the second analyte concentration measurement are abnormal based on the comparison, remove abnormal measurements associated with movement by the wearer; and
  if the first analyte concentration measurement and the second analyte concentration measurement are not determined to be abnormal based on the comparison, obtain a first analyte concentration of the first analyte and a second analyte concentration of the second analyte based at least on an assessment of the first analyte concentration measurement and the second analyte concentration measurement in a frequency domain.

* * * * *